(12) United States Patent
Haffner et al.

(10) Patent No.: US 10,416,439 B2
(45) Date of Patent: Sep. 17, 2019

(54) BOROSCOPE SHEATH

(71) Applicant: ANSALDO ENERGIA SWITZERLAND AG, Baden (CH)

(72) Inventors: Ken Yves Haffner, Baden (CH); Sanjiv Kumar Mishra, Neuenhof (CH); Etienne Louis Laprais, Nussbaumen (CH)

(73) Assignee: ANSALDO ENERGIA SWITZERLAND AG, Baden (CH)

( * ) Notice: Subject to any disclaimer, the term of this patent is extended or adjusted under 35 U.S.C. 154(b) by 310 days.

(21) Appl. No.: 15/383,639

(22) Filed: Dec. 19, 2016

(65) Prior Publication Data

US 2017/0176737 A1    Jun. 22, 2017

(30) Foreign Application Priority Data

Dec. 17, 2015 (EP) .................................. 15200770

(51) Int. Cl.
*G01N 21/00* (2006.01)
*G02B 23/24* (2006.01)
*F01D 21/00* (2006.01)
*F22B 37/00* (2006.01)
(Continued)

(52) U.S. Cl.
CPC ....... *G02B 23/2492* (2013.01); *F01D 21/003* (2013.01); *F01D 25/24* (2013.01); *F22B 37/003* (2013.01); *G01N 21/954* (2013.01); *F05D 2220/31* (2013.01); *F05D 2220/32* (2013.01); *F05D 2260/83* (2013.01)

(58) Field of Classification Search
USPC ...................................... 356/241.1
See application file for complete search history.

(56) References Cited

U.S. PATENT DOCUMENTS 5,327,880 A * 7/1994 Harley ................... G02B 23/26
356/241.4
7,662,091 B2   2/2010 Bagley et al.
(Continued)

FOREIGN PATENT DOCUMENTS

| JP | 2008-281613 A | 11/2008 |
| WO | 2012/148233 A2 | 11/2012 |
| WO | 2014/031955 A1 | 2/2014 |

OTHER PUBLICATIONS

The extended European Search Report dated Jun. 28, 2016, by the European Patent Office in corresponding European Patent Application No. 15200770.4-1504. (8 pages).

*Primary Examiner* — Rodney E Fuller
(74) *Attorney, Agent, or Firm* — Buchanan Ingersoll & Rooney PC (57) ABSTRACT

A boroscope sheath is disclosed for providing a boroscope with temperature protection during a boroscope inspection of a machine such as a gas turbine or a steam turbine. The boroscope sheath includes an elongate tube having a wall extending from a front end to a back end and around a central bore configured and arranged to allow removable insertion of a boroscope cooling channels extend in the wall. The boroscope sheath can be held in a first position relative to the machine when the machine is in use and moved to a second position relative to machine for inspection. Part of the boroscope sheath remain in the machine during use of the machine.

14 Claims, 9 Drawing Sheets

(51) Int. Cl.
*G01N 21/954* (2006.01)
*F01D 25/24* (2006.01)

(56) References Cited

U.S. PATENT DOCUMENTS

| | | | |
|---|---|---|---|
| 2002/0101508 A1* | 8/2002 | Pollack | G01N 21/8507 |
| | | | 348/85 |
| 2004/0216468 A1 | 11/2004 | Hatcher | |
| 2006/0038988 A1 | 2/2006 | Thermos | |
| 2006/0146127 A1 | 7/2006 | Bagley et al. | |
| 2011/0069165 A1* | 3/2011 | Zombo | F01D 21/003 |
| | | | 348/82 |
| 2017/0297156 A1* | 10/2017 | Kell | B23B 45/005 |

* cited by examiner

BOROSCOPE SHEATH

TECHNICAL FIELD

The present disclosure relates to boroscope sheaths for gas turbines or steam turbines, particularly horoscope sheaths with one or more cooling channels.

BACKGROUND OF THE INVENTION

Gas turbines and steam turbines are regularly inspected to ascertain the state of various parts and surfaces that are liable to deterioration. Most inspections require the gas turbine or steam turbine to be shut down first. An example of this is in the turbine of gas turbines, where a large number of parts such as blades, vanes and seals are subject to extreme conditions such as high temperatures, corrosive atmospheres and high loads. Such parts tend to need regular inspection to check for deterioration or damage but are deep inside a fully assembled gas turbine, and as a result using a boroscope (borescope) may be the most practical way of inspecting these parts.

Although boroscopes are useful for inspection in various places in gas turbines and steam turbines, boroscopes are normally limited to use in low temperatures. Gas turbines and steam turbines, however, normally operate at temperatures of many hundreds of degrees Celsius, and after shut down larger gas turbines and steam turbines can take hours or even days to cool down to a temperature low enough for a horoscope. This tends to result in a long period of waiting between shut down of a gas turbine or steam turbine and inspection using a horoscope. Time spent waiting during an inspection is time during which a gas turbine or steam turbine is offline and not available for use, which is expensive. It has been appreciated, therefore, that it would be advantageous to reduce this waiting time.

SUMMARY OF THE INVENTION

A first aspect provides a horoscope sheath for providing a horoscope with temperature protection during a boroscope inspection of a machine, the horoscope sheath comprising an elongate tube extending from a front end of the boroscope sheath to a back end of the boroscope sheath, the elongate tube comprising a wall extending from the front end to the back end and extending around a central bore, the central bore being configured and arranged to allow removable insertion of a horoscope into the central bore, one or more cooling channels extending in the wall, and means for holding the horoscope sheath in a first position relative to the machine when the machine is in use and for moving the horoscope sheath to a second position relative to the machine for inspection, and in which at least part of the horoscope sheath is configured and arranged to remain in the machine during use of the machine. The machine is preferably a gas turbine or a steam turbine.

This can provide a number of advantages. With this horoscope sheath, a boroscope can be protected within a machine to keep the boroscope below a set temperature, to protect the boroscope from a higher temperature inside the machine. As a result, the machine can be inspected using a boroscope while the machine is still above the set temperature (and above ambient temperature), by providing a lower temperature environment within the elevated temperature environment of the machine. For example, the boroscope sheath can reduce or avoid the need to let an entire engine (gas or steam turbine) cool before inspection, and can therefore reduce inspection time by hours. Inspection can be performed after rotor barring. The flexibility and ease of inspection can be improved, and the time interval that a gas turbine or steam turbine is stopped during a regular inspection can be reduced. Providing apparatus in which at least part of the boroscope sheath is configured and arranged to remain in the gas turbine or steam turbine during use of the gas turbine or steam turbine can help limit the health and safety challenges that result from taking out hot plugs from existing inspection holes.

In one embodiment, the elongate tube comprises a hole through the wall, and wherein a part of the machine can be inspected through the hole when the boroscope sheath is in the second position. In one embodiment, the hole is proximate the front end of the elongate tube. In one embodiment, at least part of the boroscope sheath is manufactured by selective laser melting.

In one embodiment, the means for holding the boroscope sheath in a first position relative to the machine when the machine is in use and for moving the boroscope sheath to a second position relative to the gas turbine or steam turbine for inspection comprises a tip sheath extending around the elongate tube to hold the boroscope sheath in place in the first position and a spring for attaching the tip sheath to the machine.

A second aspect provides a gas turbine or a steam turbine comprising the boroscope sheath described above. In one embodiment, the gas turbine or steam turbine comprises a turbine with a hot gas path and the boroscope sheath is configured and arranged to extend into the hot gas path for inspection.

A third aspect provides a method of cooling a boroscope sheath for a machine, the boroscope sheath comprising an elongate tube extending from a front end of the boroscope sheath to a back end of the horoscope sheath, the elongate tube comprising a wall extending from the front end to the back end and extending around a central bore, the central bore being configured and arranged to allow removable insertion of a boroscope into the central bore, one or more cooling channels extending in the wall, and means for holding the horoscope sheath in a first position relative to the machine when the machine is in use and for moving the horoscope sheath to a second position relative to the machine for inspection, and in which at least part of the horoscope sheath is configured and arranged to remain in the machine during use of the machine, the method comprising the steps of injecting cooling gas into the central bore and/or into at least one of the one or more cooling channels in a first step, and in a second step, injecting cooling liquid into at least one of the one or more cooling channels. The machine is preferably a gas turbine or a steam turbine.

In one embodiment, cooling gas is also injected into the central bore and/or at least one of the one or more cooling channels during the second step. In one embodiment, the first step is finished and the second step is started when a temperature of the horoscope sheath is below a set point, preferably 100 degrees Celsius. In one embodiment, the boroscope sheath is moved from the first position to the second position before the first step.

A fourth aspect provides a method of inspecting a part of a machine, comprising the steps of cooling a horoscope sheath using the method described above, moving a boroscope sheath from the first position to the second position, and inspecting a part of the machine through a hole in the boroscope sheath with a boroscope. The machine is preferably a gas turbine or a steam turbine. This method can allow inspection for damage, for example spallation, cracking or corrosion of blades in the turbine of a gas turbine.

A fifth aspect provides a method of manufacturing a boroscope sheath for a machine, the boroscope sheath comprising an elongate tube extending from a front end of the boroscope sheath to a back end of the boroscope sheath, the elongate tube comprising a wall extending from the front end to the back end and extending around a central bore, the central bore being configured and arranged to allow removable insertion of a boroscope into the central bore, one or more cooling channels extending in the wall, and means for holding the boroscope sheath in a first position relative to the machine when the machine is in use and for moving the boroscope sheath to a second position relative to the machine for inspection, and in which at least part of the boroscope sheath is configured and arranged to remain in the machine during use of the gas turbine or steam turbine, in which at least part of the boroscope sheath is manufactured using selective laser melting. The machine is preferably a gas turbine or a steam turbine. Selective laser melting can enable smaller diameter boroscope sheaths than other manufacturing technologies. Smaller boroscope sheaths can take up less space, and can fit in smaller inspection holes in existing gas and steam turbines. Smaller boroscope sheaths can also cool faster.

BRIEF DESCRIPTION OF THE DRAWINGS

An embodiment of the invention will now be described by way of example only and with reference to the accompanying drawings in which.

DETAILED DESCRIPTION OF THE PREFERRED EMBODIMENTS

Figures 1, 2:
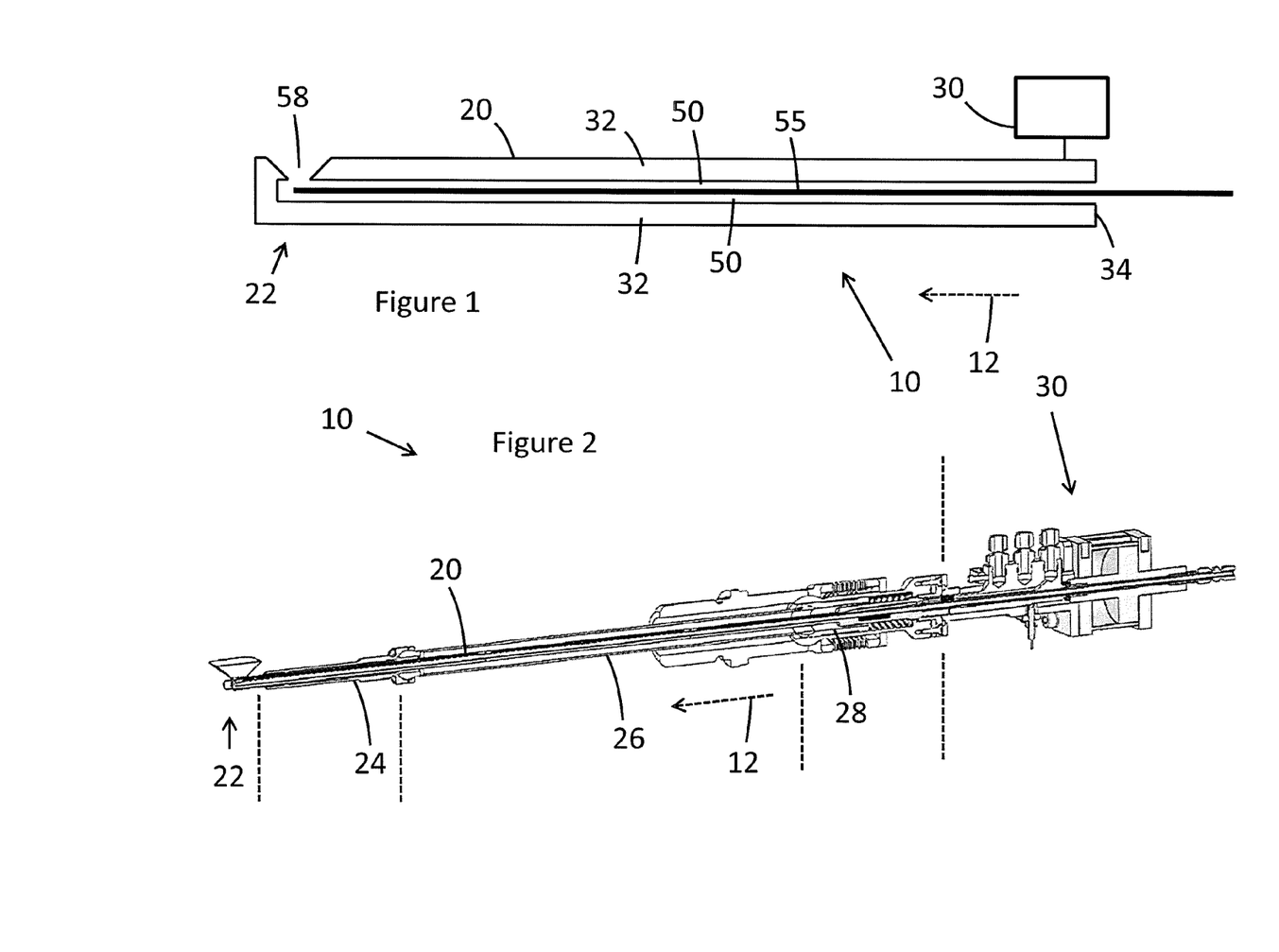
FIG. 1 shows a simplified cross-section of a boroscope system.
FIG. 2 shows a perspective and cross-section view of a boroscope system with a boroscope sheath, a guide and a boroscope sheath support system.

FIG. 1 shows a simplified cross-section of a horoscope system 10. The horoscope system comprises a horoscope sheath (horoscope cooling tube) 20, a horoscope (borescope) 55 and a horoscope sheath support system 30. The horoscope sheath comprises an elongate tube with a wall 32 extending from a back end 34 to a tip portion 22 in an axial direction 12. The wall extends around a central bore 50. The horoscope can be fed through the central bore from the back end to the tip portion to place it as shown in FIG. 1. The tip portion comprises a hole 58 through which a camera in the horoscope can be used for inspection. At the back end, the horoscope sheath is connected to a support system 30. At least one cooling channel (not shown) is supplied from the support system and extends through the wall from the back end to the tip portion.

Figure 3:
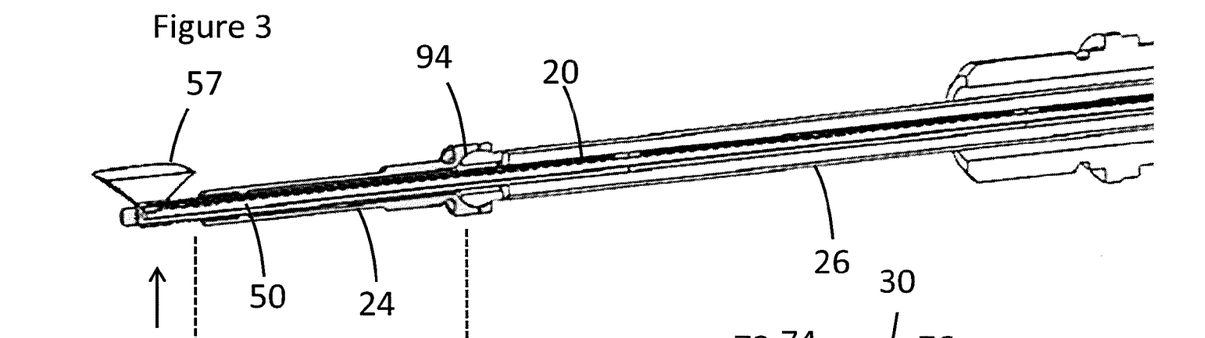
FIGS. 3 and 4 show an enlarged version of FIG. 2.
Figure 4:
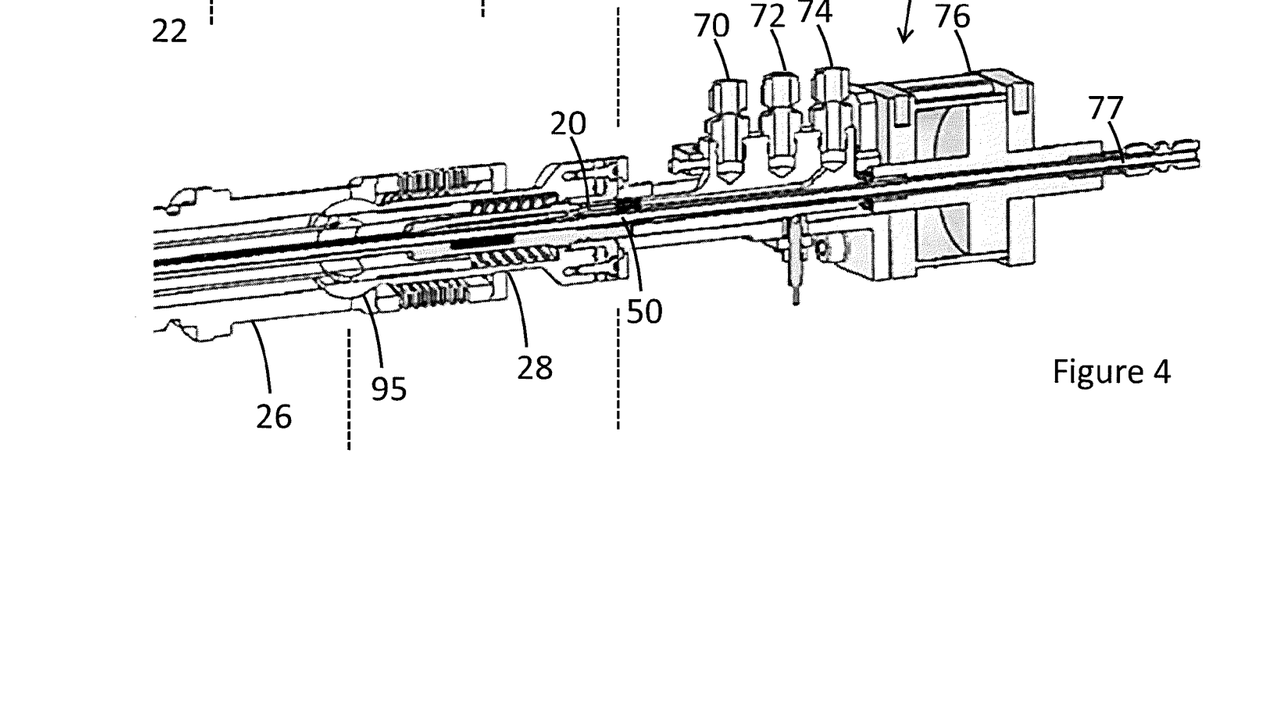

FIG. 2 shows a more detailed example of a horoscope system 10 within the context of some adjacent parts of the gas turbine. FIGS. 3 and 4 show a zoomed-in view of FIG. 2. In FIG. 2, a horoscope sheath 20 and a horoscope sheath support system 30 can be seen. A guide comprising a front piece (plug) 24, a middle piece 26 and a back piece 28 extends around the horoscope sheath. The dashed lines roughly indicate the extent of the different parts. The tip portion 22 of the horoscope sheath can be seen extending beyond the front piece 24. When in use, a boroscope (not shown) is inserted through the horoscope sheath support system and the horoscope sheath.

FIGS. 3 and 4 show an enlarged view of the system of FIG. 2. In FIG. 3, a camera visibility cone extends from the tip portion 22; this is not a physical part but shows the viewing angles available from the horoscope from inside the boroscope sheath. The central bore 50 in the horoscope is also shown. In FIG. 4, details of the support system 30 can be seen, which will be described in more detail below.

Figures 5, 6, 7, 8:
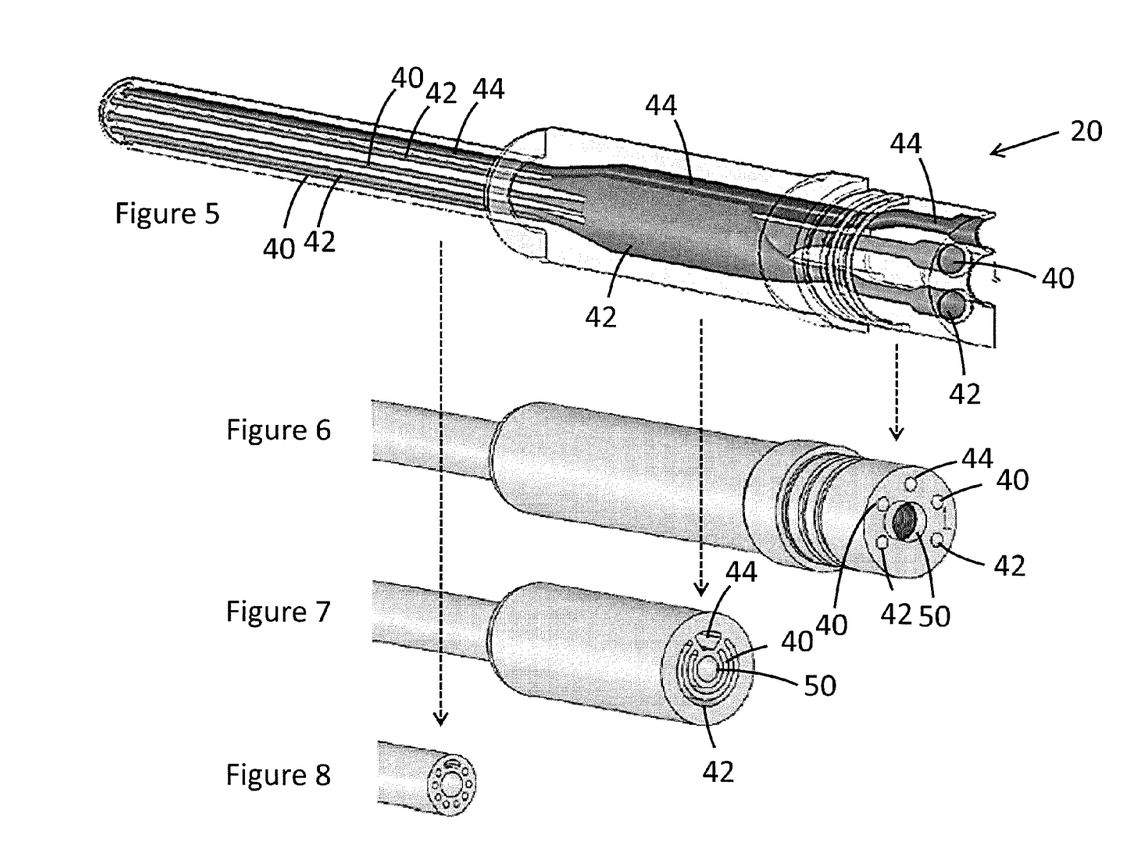
FIG. 5 shows a partly see-through perspective view of part of a boroscope sheath, showing the cooling channels.
FIG. 6 shows a perspective view of part of the boroscope sheath of FIG. 5, including a cross-section of the boroscope sheath.
FIGS. 7 and 8 show perspective views as in FIG. 6 with cross sections at different points along the boroscope sheath.

FIG. 5 shows a part of a boroscope sheath 20; this roughly corresponds to the part of the boroscope sheath 20 seen in FIG. 4 inside the back piece 28 and the middle piece 26 of the guide. A number of channels 40, 42, 44 for cooling fluids can be seen. In particular, a water feed channel 40 and a water return channel 42 can be seen, along with an air feed channel 44. The channels 40, 42, 44 extend along the boroscope. The example in FIG. 5 shows the water feed and water return channels 40, 42 both entering into a chamber portion (see also FIG. 7) before splitting into two separate channels part of the way down the probe.

Figure 9:
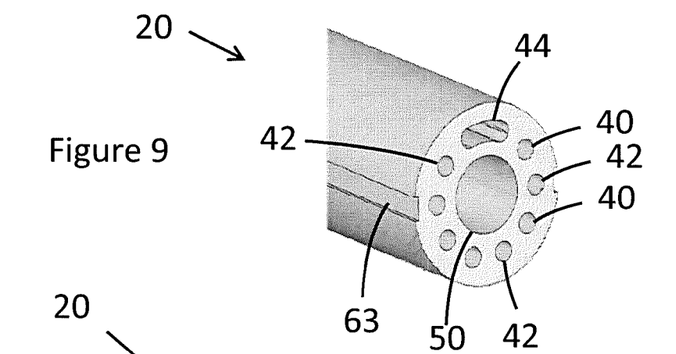
FIG. 9 shows an enlarged view of the view shown in FIG. 8.

FIGS. 6, 7 and 8 each show cross-sections of the boroscope sheath of FIG. 5, showing the evolution of the cross-sectional shape of the channels 40, 42, 44 along the boroscope sheath. The central bore 50, through which the boroscope can pass, can also be seen. FIG. 9 shows an enlarged view of FIG. 8. In FIG. 9, grooves 63 can be seen. These grooves are part of the locking system, which is described in more detail below.

Figure 10:
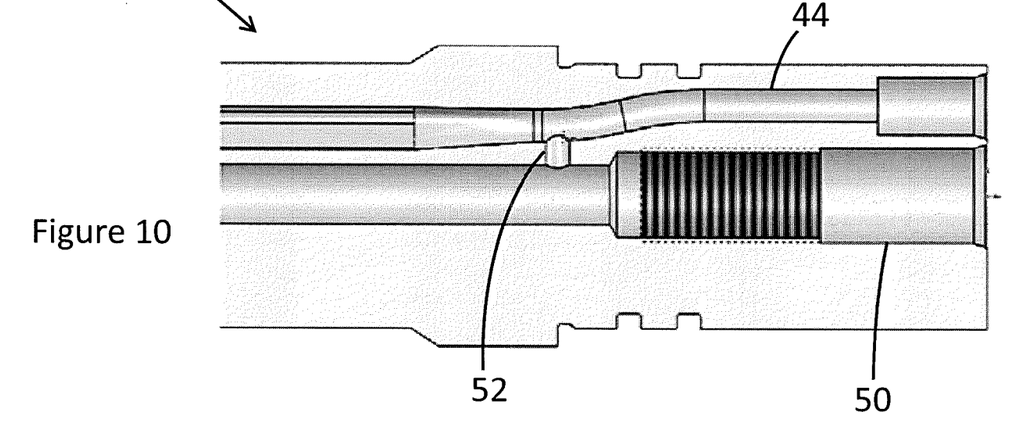
FIG. 10 shows a cross-section of part of the boroscope sheath.

FIG. 10 shows a cross-section of part of the boroscope sheath, roughly corresponding to the right half of the part of the boroscope sheath shown in FIG. 5 (i.e. the wider portion). The air feed channel 44 can be seen, along with the central bore 50. A bypass 52 extending from the air feed channel to the central bore 50 can also be seen; this allows air to pass from the air feed channel into the central bore.

Figures 11, 12:
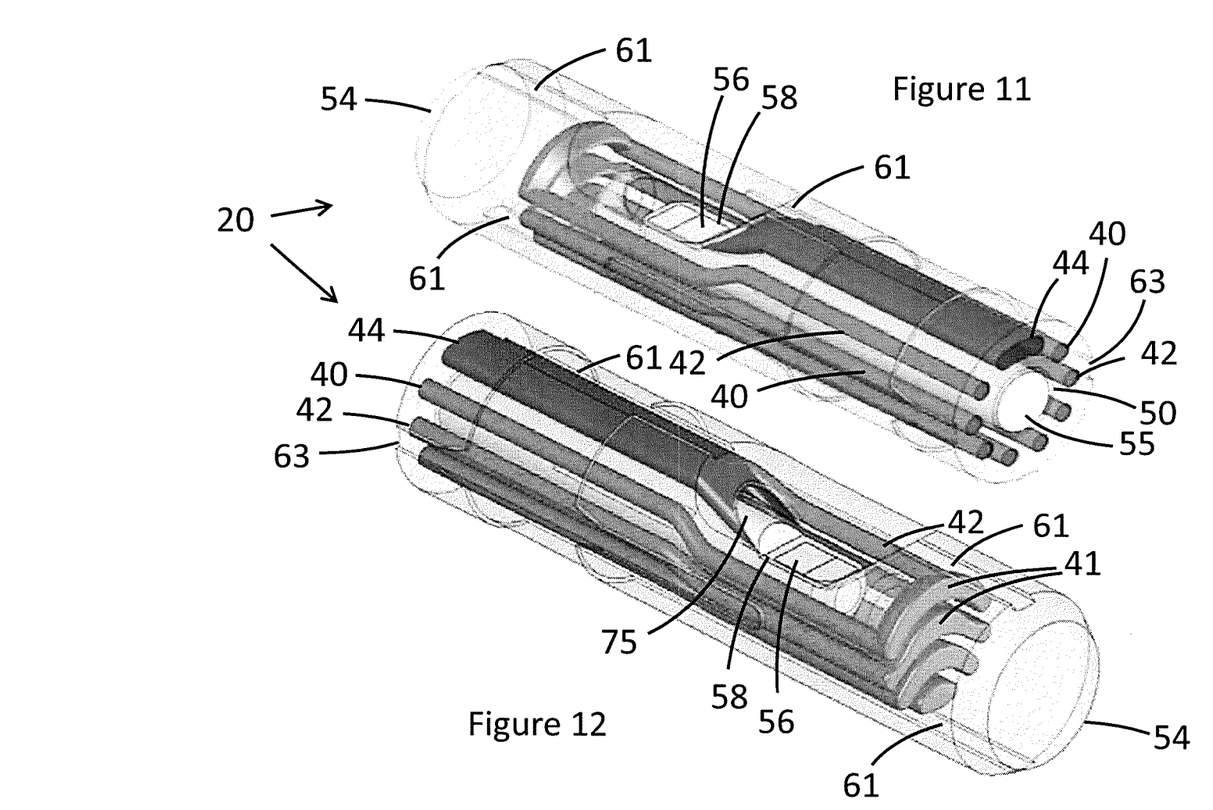
FIGS. 11 and 12 show partly see-through perspective views of the tip portion of the boroscope sheath of FIG. 5, showing the cooling channels.

FIGS. 11 and 12 show part of the tip portion 22 of the boroscope sheath 20 from different angles. The channels 40, 42, 44 can again be seen. Each water feed channel 40 is joined to a water return channel 42 by a tip water channel 41. The tip water channels 41 extend near the front end 54 of the tip portion, between the central bore 50 of the boroscope sheath 20 and the front end 54. When in use, the camera 56, which is on the end of the boroscope, is positioned to give a field of view out of a camera hole 58. The air feed channel 44 ends near the camera at the air outlet 75, and the air flow exiting the air feed channel can help provide cooling for the camera, for example by providing a cooling film of air in front of the camera, and/or help keep the boroscope camera clean.

Figure 13:
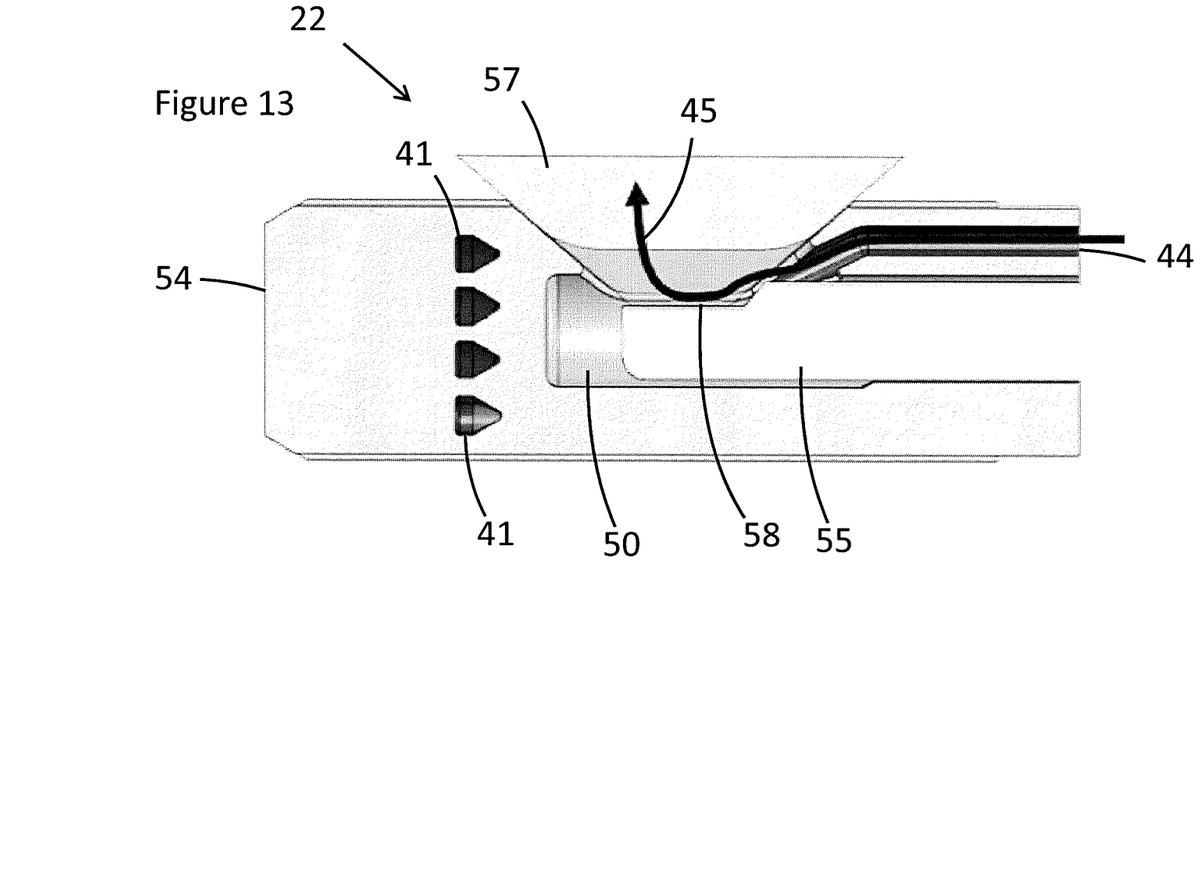
FIG. 13 shows a cross-section of part of the tip portion of the boroscope sheath.

FIG. 13 shows a cross-section of part of the tip portion 22. The path of the cooling air 45 through the air feed channel 44 and out into the area around the camera hole is shown. A camera visibility cone 57 which shows the extent of the visibility available to the camera when in use can also be seen.

Figure 14:
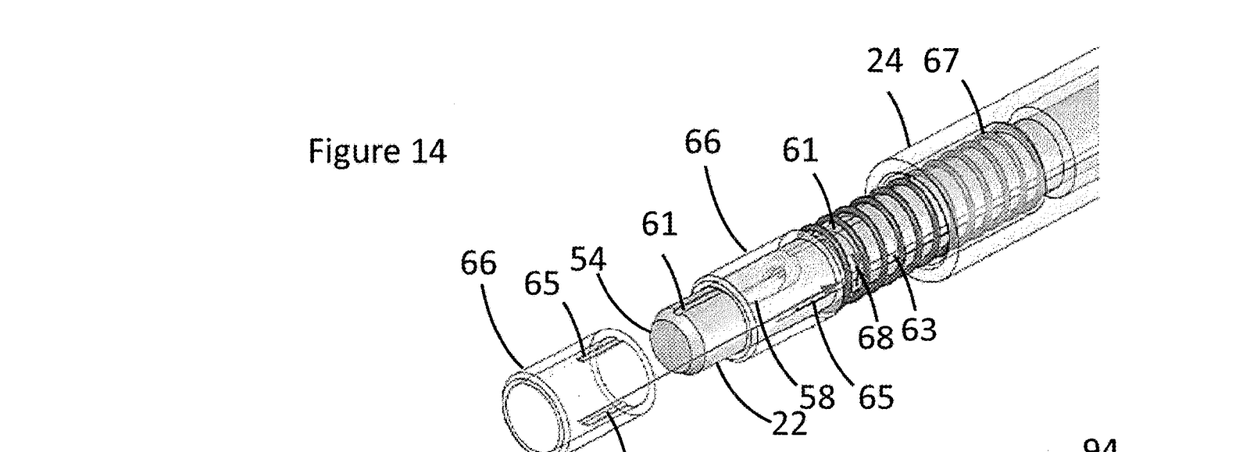
FIG. 14 shows a partly see-through perspective view of the tip portion of the horoscope sheath.
Figure 15:
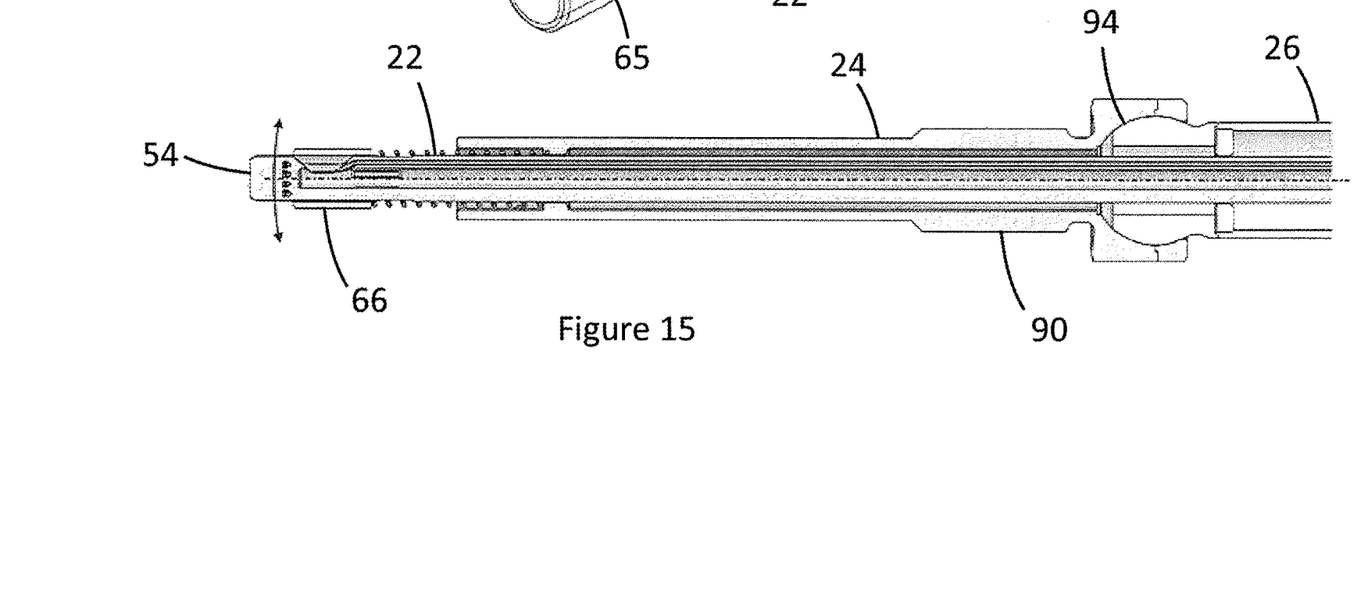
FIG. 15 shows a cross-section of part of the boroscope sheath inside the guide.

FIGS. 14 and 15 show the tip portion 22 and the front piece 24 of the guide, along with a means for holding the boroscope sheath in a first position (closed position) relative to the gas turbine or steam turbine when the gas turbine or steam turbine is in use, and for moving the boroscope sheath to a second position (open position) relative to the gas turbine or steam turbine for inspection. To explain this function in context, one example of a location where the system described herein can be used is for inspection of the blades and vanes in the turbine of a gas turbine (see FIG. 17). When the gas turbine is in use, withdrawing the boroscope sheath within the front piece of the guide can stop hot gases escaping through the central bore 50. As the camera hole 58 is on the side of the tip portion rather than on the front end 54, withdrawing the tip portion into the gas turbine (into the guide) or into a tip sheath 66 can protect the hole from hot gas ingress, even if the front end 54 and/or other parts of the boroscope sheath are still exposed to hot gases.

The mechanism in FIGS. 14 and 15 comprises a tip sheath (tip sleeve) 66 with protrusions 65 for engaging in grooves 61, 63 in the boroscope sheath 20, and a spring 67 attached to the tip sheath 66 and to the front piece 24 of the guide.

The tip sheath 66 comprises two protrusions 65 that are arranged to fit in open position and closed position grooves 61, 63 in the boroscope sheath. The groove 63 extends to near the front end 54 but does not actually reach the front end. As a result, the camera hole 58 in the boroscope sheath cannot move beyond the tip sheath 66 when the groove 63 is lined up with the one of the protrusions 65. The spring 67 keeps the tip sheath from moving away towards the front piece 24 of the guide. The boroscope sheath would remain with groove 63 lined up with one of the protrusions 65 when the gas turbine is in use.

To move the boroscope sheath 20 beyond the tip sheath 66 for inspection, the boroscope sheath is first pulled back out of the gas turbine slightly (i.e. the front end 54 is moved towards the front piece 24 of the guide) to disengage the groove 63 from the protrusions 65. The boroscope sheath is then rotated 90 degrees with the protrusions 65 in the turn slot 68 to allow the grooves 61 to engage a protrusion 65. As the grooves 61 extend all the way to the front end 54, the boroscope sheath can then extend further past the tip sheath 66 so that the camera hole 58 is beyond the tip sheath. To show the protrusions 65 more clearly and also to show the two different orientations of the tip sheath relative to the boroscope sheath, the tip sheath is shown twice, once attached to the spring 67 and with the protrusion 65 in the groove 63, and once on its own. The tip sheath on its own shows the orientation of the tip sheath necessary to engage the protrusions 65 with the groove 61.

Providing a mechanism of this kind can provide a way of moving the boroscope sheath out into the hot gas path for inspection and then returning the boroscope sheath and securing it within the front piece 24 of the guide.

Figure 16:
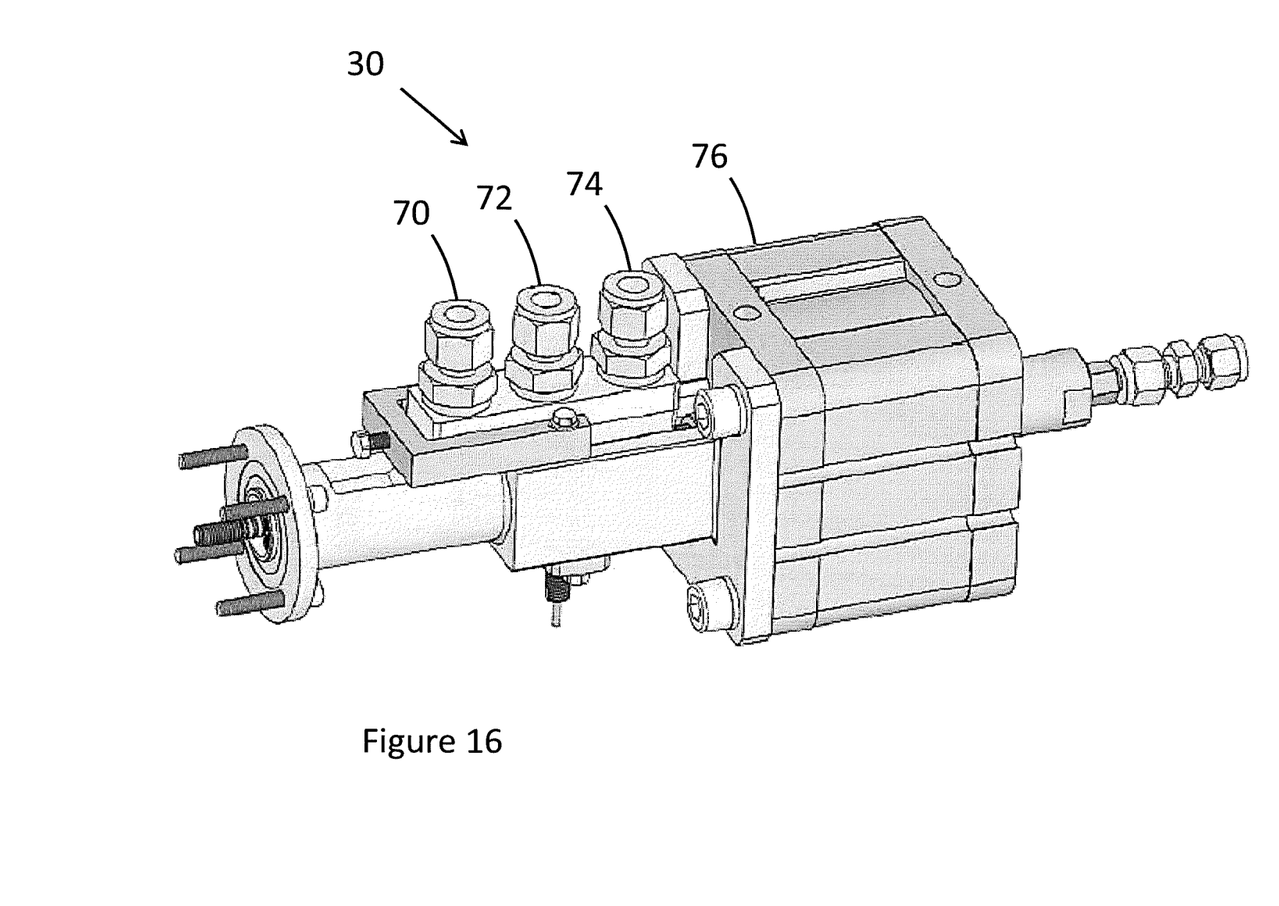
FIG. 16 shows a boroscope sheath support system.

FIG. 16 shows a boroscope sheath support system 30, as shown in cross section in FIGS. 2 and 4. The support system comprises a water inlet 70, a water outlet 72, an air inlet 74 and a pneumatic device 76. The pneumatic device can be used to control the extent to which the boroscope sheath extends beyond the end of the guide (beyond the front piece). In this example, the boroscope can pass through the central bore 77 of the support system and into the boroscope sheath, as can be seen in FIG. 4.

Figure 17:
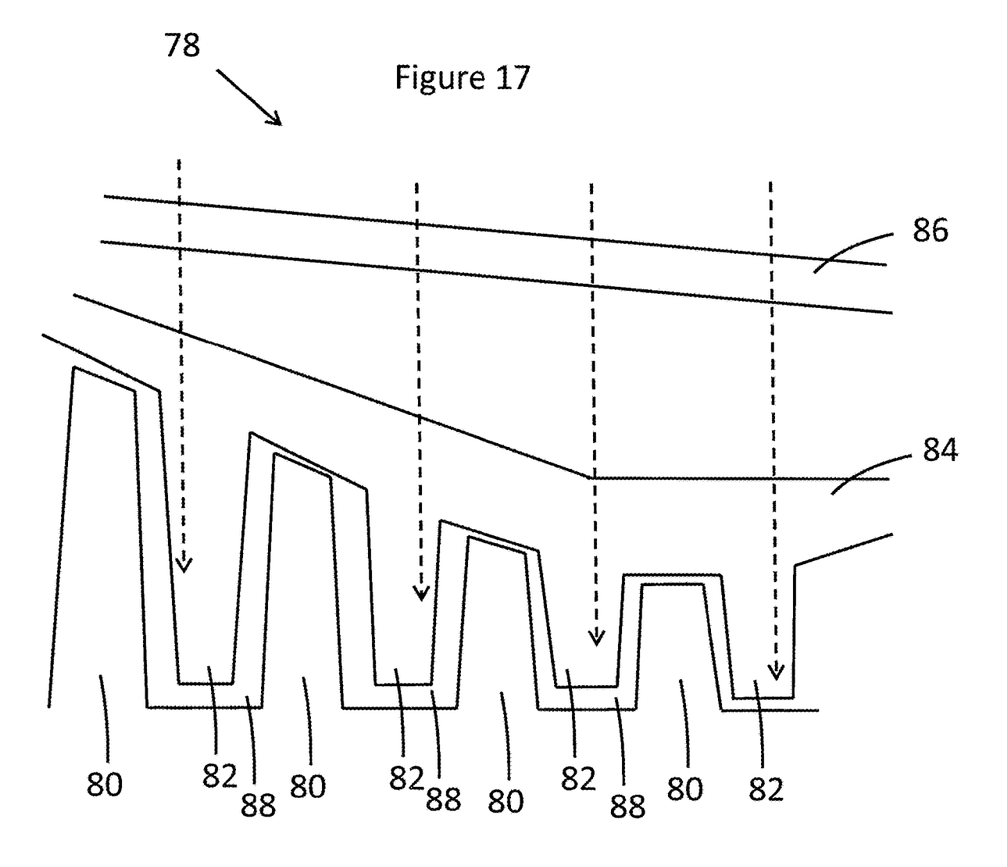
FIG. 17 shows a simplified cross-section of part of the turbine of a gas turbine.

FIG. 17 shows an outline of a cross-section of part of the turbine of a gas turbine. Blades 80, vanes 82, a vane carrier 84 and an outer housing 86 are shown. The dashed arrows show where holes could be provided through the outer housing and the vane carrier to allow a guide, a boroscope sheath and a boroscope as described above to be inserted into the turbine.

A gas turbine will typically run for a set amount of time before being inspected and also repaired if necessary. Before an inspection, the gas turbine is shut down.

In an example method using the system shown in FIGS. 2 to 4, there would typically be no need to first insert the guide 24, 26, 28 and the boroscope sheath 20 into the gas turbine, as these parts would remain in the gas turbine during use of the gas turbine. The support system, if one is included, could also be left in place during use of the gas turbine, or could alternatively be removed between inspections.

The first step would therefore typically be to unlock and extend the boroscope sheath into the part of the turbine that is to be inspected. This allows cooling air to be injected into the boroscope sheath and to pass out of the boroscope sheath through the camera hole 58 and the air outlet 75. Additionally or alternatively, air can be passed through the water feed channel 40 and water return channel 42. For as long as only the water channels 40, 42 are used, it is not necessary to extend the boroscope sheath, although the boroscope sheath must eventually be extended to allow for inspection using the boroscope 55.

The next step would therefore normally be to inject cooling air into at least one of the cooling channels 40, 42, 44 and/or into the central bore. This air would cool the boroscope sheath. Typically, cooling air should be injected until the temperature of the boroscope sheath (at least in the cooling channels where water will be injected) is below a set point, such as 100 degrees Celsius. This avoids boiling of the water when the water is injected. The length of time needed for the boroscope sheath to drop below 100 degrees Celsius can be determined directly or indirectly, for example by using a sensor or sensors in the boroscope sheath, during a test phase or by computer modeling. Such a sensor may be inserted prior to the insertion of the boroscope and then removed again to insert the boroscope, or may be permanently attached to the boroscope sheath or the gas turbine. A set length of time may also be used. For example, the measured temperature could be the temperature of cooling air exiting the water return channel 42 or the temperature of cooling air exiting through the camera hole 58 or the air outlet 75.

After the step during which only cooling air is injected into the boroscope sheath, the next step is started, in which both cooling water and cooling air are injected into the boroscope sheath. During this step air passes through the air feed channel 44 and water passes through the water feed channel 40 and water return channel 42. Air can also be fed through the central bore 50, either directly at the back end 34 or via a bypass 52 from the air feed channel 44 (see FIG. 10). During this step, the temperature of the boroscope sheath is further reduced to below a second set point, for example to 40 degrees Celsius. This second set point is a temperature at which the boroscope can safely be inserted into the boroscope sheath. The length of time needed for this step can be determined directly or indirectly as described above for the cooling air injection step.

By this point, the boroscope sheath will normally have already been extended as described above. The boroscope can then be inserted into the boroscope sheath and inspection can take place. The boroscope sheath can be inserted a pre-defined length, or may be able to extend to any length required for the inspection, providing a greater field of view. The boroscope sheath can generally also be rotated relative to the the axial direction 12 to allow for a 360 degree field of view around the boroscope sheath. The boroscope sheath can generally be moved from the back end 34, either directly (manually) or remotely.

During inspection, water may continue to circulate through the water channels 40, 42 and/or air may continue to circulate through the air feed channel 44 and/or the central bore 50. As only the local area will have been cooled rather than the entire gas turbine, it is generally necessary to continue to cool the boroscope sheath during inspection, although the cooling water and/or air flow rate that is necessary may be reduced.

In one example, the initial central bore air temperature before cooling is 800 degrees Celsius and the final temperature after cooling is 40 degrees Celsius. In one example, the cooling phase (between starting to cool the horoscope sheath and inserting the boroscope) lasts up to 15 minutes, preferably up to 5 minutes and particularly between 2 and 4 minutes.

A boroscope sheath as described above may be retrofitted into an existing gas turbine or steam turbine.

In a method of manufacturing a horoscope sheath, part or all of the boroscope sheath may be manufactured using selective laser melting (SLM). In particular, the elongate tube may be manufactured using SLM. The support system may also be manufactured using SLM. Other appropriate manufacturing methods may also be used. The space available for a horoscope sheath in the gas turbine can be very restricted, particularly when retrofitting an existing turbine, and SLM can be particularly useful in enabling the manufacture of boroscope sheaths for such applications.

The boroscope system 10 is shown in FIG. 2 with various modular parts. Alternatively, two or more of the parts could be integrated together within the same part, and/or one or more of the parts could be manufactured as separate parts.

The boroscope sheath 20 may be a single integral part as shown in FIG. 1, or may comprise a two or more parts attached together. In one example, the boroscope sheath comprises three parts, namely a front part, a middle part and a back part. In such an example, a single front part and a single back part could be provided, along with several different middle parts of different lengths to fit different places in a gas turbine. In a boroscope sheath with two or more parts, the front part of the boroscope sheath (the part adjacent to the hot gas path, for example) could remain in the gas turbine during use of the gas turbine, with the other part or parts of the boroscope sheath only being inserted before inspection and being removed again after inspection. This can be useful from a health and safety point of view, as it avoids the need to remove a plug from adjacent to a hot gas path.

The boroscope sheath 20 would generally have a circular cross-section in the plane perpendicular to the axial direction 12, although other shapes are also possible, for example to match the shape of the surrounding guide 24, 26, 28 and/or the shape of gas turbine. The boroscope sheath may also vary in width along its length, as shown in FIG. 10 for example. A typical diameter for the boroscope sheath at the tip portion would be between 5 mm and 25 mm, preferably between 8 mm and 15 mm, and particularly 10 mm. The cooling channels 40, 41, 42, 44 could also vary in size, and typical diameters for the cooling channels would be between 0.5 mm and 2 mm, preferably between 0.8 mm and 1.5 mm and particularly 1.0 mm.

The tip portion 22 is a portion of the boroscope sheath at the end where the camera hole 58 is situated. It includes the very front of the boroscope sheath (the front end 54) along with a portion of the boroscope sheath, such as the portion that protrudes beyond the front piece 24 of the guide in FIGS. 14 and 15. The back end 34 is the very back of the boroscope sheath, where the boroscope sheath is joined to the support system 30 in FIG. 2 (although in some embodiments the support system does not have to be fitted right at the back end of the boroscope sheath). In an example, after the boroscope sheath is installed in the turbine 78 in FIG. 17, the tip portion 22 and the front end 54 would be adjacent to or in the hot gas path 88 and the back end 34 would be in or outside the vane carrier 84 or the outer housing 86. The support system, if necessary, would generally be outside the outer housing.

The guide comprising front piece 24, middle piece 26 and back piece 28 as described above would typically be fitted into a gas turbine to provide a guide for the boroscope sheath. The guide could be attached to the vane carrier 84 and/or the outer housing 86, for example. A combination of the front piece (plug) 24 of the of the guide and the boroscope sheath in its closed position would normally stop hot gas ingress during use of a gas turbine or steam turbine so as to avoid unnecessary pressure loss. Closing the boroscope sheath can block the camera hole 58 and air outlet 75.

The guide could be one, two, four or more pieces rather than being three pieces, and could extend around the boroscope sheath along part or all of its length. The guide is optional, and the boroscope sheath may alternatively be fitted directly into a gas turbine. The separate pieces of the guide could be fitted together in various ways; one example is the ball and socket joint 94 between front piece 24 and middle piece 26 that is visible in FIGS. 3 and 15 and the ball and socket joint 95 between middle piece 26 and back piece 28 that is visible in FIG. 4. The guide could also comprise two or more parts spaced apart from one another. The guide can also be fitted to the gas turbine in various ways; one example would be using a thread on the guide and an accompanying thread on the gas turbine. A thread could be included at a thread position 90 on the front piece 24 of the guide in FIG. 15, for example.

The support system 30 may include a central bore 77 as in FIG. 4, or may alternatively not include a central bore, with the boroscope passing to one side of the support system. The support system would typically provide an interface for any necessary external interfaces, for example cooling fluid pipes, sensor wiring, control valves and control wiring. As such, the support system per se is optional, and cooling fluid pipes could be fitted directly to the boroscope sheath, for example.

The support system can also provide control over the placement of the horoscope and/or horoscope sheath relative to the guide (or relative to the gas turbine), for example with a pneumatic device 76. The horoscope and horoscope sheath positions could also be adjusted manually. To allow for greater visibility using the boroscope, the boroscope sheath could be rotatable to allow for a change in the field of view. The tip portion of the horoscope sheath could also be flexible to allow for further changes in the field of view. Providing multiple camera holes 58 in the horoscope sheath, for example at different locations in the axial direction and/or around the circumference of the boroscope sheath, could also provide additional fields of view.

The wall 32 extends around the central bore 50 and is normally straight, extending in an axial direction 12 (see FIGS. 1 and 2). The central bore 50 is also normally straight and extending in the axial direction 12. The central bore would generally be cylindrical (so with a circular cross section perpendicular to the axial direction 12), although other shapes are possible. Protrusions may be provided on the wall extending into the central bore to support a horoscope and to hold a horoscope away from the wall. This can further reduce heating of the horoscope by leaving a gap between the wall and the boroscope, and can also allow cooling air to pass between the horoscope and the wall.

Normally, most of the cooling channels in the wall will extend from the back end to the tip portion. Water feed channels 40, water return channels 42 and air feed channels 44 will normally extend in the axial direction 12. Tip water channels 41 will typically extend in a plane perpendicular to the axial direction 12. The channel setup shown in the examples above may be modified, and various other numbers, shapes and combinations of channel are possible. Channel splitting as shown in FIG. 5 is also optional, and some or all of the channels could also be split in other ways. The air outlet 75 and the bypass 52 could also be placed elsewhere, and multiple air outlets and bypasses could be provided rather than just one.

The systems described above use water and air as cooling fluids. Another liquid could be used instead of water, and another gas could be used instead of air, such as nitrogen or carbon dioxide. Use of a liquid with a higher boiling temperature than water would allow liquid cooling to commence at a higher temperature.

The front end 54 is normally configured and arranged to be in contact with a hot gas path when the gas turbine or steam turbine is in use. To this end, the front end may be coated with a thermal barrier coating (TBC), as may other parts that are exposed to hot gases such as the tip sheath 66. Alternatively or additionally, parts that are exposed to hot gases may be made of a material with a greater heat tolerance than parts further from hot gas exposure. The front end is normally closed, as can be seen in FIGS. 1, 11 and 12 for example.

The boroscope 55 may be any appropriate horoscope that fits within the boroscope sheath. The camera 56 could be a camera for taking still images or a videocamera, for example.

The camera hole 58 described herein extends through the wall 32 in the tip portion. It is near but not at the front end 54, and extends through the wall in a radial direction relative to the axial direction 12. The camera hole could also be provided at the front end 54, along with a shutter for the hole so that the hole could be closed when the gas turbine is in use. The camera hole could be covered with a high temperature glass. Camera holes could also be provided elsewhere on the boroscope sheath.

The mechanism shown in FIGS. 14 and 15 is merely an example, and other means for removably holding the boroscope sheath in a closed (locked) position can also be used. For example, the boroscope sheath could clip into or be screwed into the guide. Various alterations could also be made to the setup shown in FIGS. 14 and 15; for example, one or more of each of the open position grooves 61, closed position grooves 63 and protrusions 65 may be provided, with two of each provided in the examples shown above, and the grooves could be separated by angles other than 90 degrees.

A gas turbine comprises a compressor, a combustor downstream of the compressor and a turbine downstream of the combustor. FIG. 17 shows several locations in the turbine 78 of a gas turbine in which the apparatus described above could be used. Various other areas in a gas turbine may also benefit from a horoscope sheath of this nature, including within the compressor and the combustor. Steam turbines also comprise a turbine with a hot gas path, although the hot gas is steam instead of flue gas. The horoscope sheath described above has primarily been described in the context of a gas turbine, but the concept can generally be extended to other machines which operate at temperatures above ambient temperature and where horoscope inspection may be needed, such as steam turbines, without major changes. As with gas turbines, the boroscope sheath described above has potential applications in various places in a steam turbine, such as for inspection of vanes and blades in the turbine of a steam turbine.

Various modifications to the embodiments described are possible and will occur to those skilled in the art without departing from the invention which is defined by the following claims.

| REFERENCE NUMERALS | |
|---|---|
| 10 | boroscope system |
| 12 | axial direction |
| 20 | boroscope sheath |
| 22 | tip portion |
| 24 | front piece |
| 26 | middle piece |
| 28 | back piece |
| 30 | support system |
| 32 | wall |
| 34 | back end |
| 40 | water feed channel (cooling channel) |
| 41 | tip water channel (cooling channel) |
| 42 | water return channel (cooling channel) |
| 44 | air feed channel (cooling channel) |
| 45 | cooling air |
| 50 | central bore |
| 52 | bypass |
| 54 | front end |
| 55 | horoscope |
| 56 | camera |
| 57 | camera visibility cone |
| 58 | camera hole |
| 61 | open position groove |
| 63 | closed position groove |
| 65 | protrusion |
| 66 | tip sheath (tip sleeve) |
| 67 | spring |
| 68 | turn slot |
| 70 | water inlet |
| 72 | water outlet |
| 74 | air inlet |
| 75 | air outlet |
| 76 | pneumatic device |
| 77 | central bore |
| 78 | turbine |
| 80 | blade |
| 82 | vane |
| 84 | vane carrier |
| 86 | outer housing |
| 88 | hot gas path |
| 90 | thread position |
| 94 | ball and socket joint |
| 95 | ball and socket joint |

The invention claimed is:

1. A boroscope sheath for providing a boroscope with temperature protection during a boroscope inspection of a machine, the boroscope sheath comprising:
   an elongate tube extending from a front end of the boroscope sheath to a back end of the boroscope sheath, the elongate tube having a wall extending from the front end to the back end and extending around a central bore, the central bore being configured and arranged to allow removable insertion of a boroscope into the central bore;
   a plurality of cooling channels extending in the wall, the plurality of cooling channels including a gas cooling channel configured to circulate gas and a liquid cooling channel configured to circulate gas and liquid; and
   means for holding the boroscope sheath in a first position relative to a machine when the machine is in use and for moving the boroscope sheath to a second position relative to the machine for inspection, at least part of the boroscope sheath is configured and arranged to remain in the machine during use of the machine.

2. The boroscope sheath of claim 1, in which the elongate tube comprises:
   a hole through the wall, to allow a part of the machine to be inspected through the hole when the boroscope sheath is in the second position and an air outlet for the gas cooling channels arranged proximate the hole and configured to direct cooling air onto the boroscope sheath.

3. The boroscope sheath of claim 2, in which the hole is proximate the front end of the elongate tube.

4. The boroscope sheath of claim 1, in which at least part of the boroscope sheath a selectively laser melted part.

5. The boroscope sheath of claim 1, in which the means for holding the boroscope sheath in a first position relative to the machine when the machine is in use and for moving the boroscope sheath to a second position relative to the machine for inspection comprises:
   a tip sheath extending around the elongate tube to hold the boroscope sheath in place in the first position and a spring for attaching the tip sheath to the machine.

6. A gas turbine or a steam turbine comprising:
   the boroscope sheath of claim 1.

7. The gas turbine or steam turbine of claim 6, in which the gas turbine or steam turbine comprises:
   a turbine with a hot gas path, and the boroscope sheath is configured and arranged to extend into the hot gas path for inspection.

8. A method of cooling a boroscope sheath for a machine, the boroscope sheath having an elongate tube extending from a front end of the boroscope sheath to a back end of the boroscope sheath, the elongate tube having a wall extending from the front end to the back end and extending around a central bore, the central bore being configured and arranged to allow removable insertion of a boroscope into the central bore, one or more cooling channels extending in the wall, and means for holding the boroscope sheath in a first position relative to the machine when the machine is in use and for moving the boroscope sheath to a second position relative to the machine for inspection, wherein at least part of the boroscope sheath is configured and arranged to remain in the machine during use of the machine, the method comprising:
   injecting cooling gas into the central bore and/or into at least one of the one or more cooling channels in a first step; and
   in a second step, injecting cooling liquid into at least one of the one or more cooling channels.

9. The method of claim 8, which comprises, during the second step;
   injecting cooling gas into the central bore and/or at least one of the one or more cooling channels.

10. The method of claim 8, wherein the first step is finished and the second step is started when a temperature of the boroscope sheath is below a set point.

11. The method of claim 8, comprising:
    moving the boroscope sheath from the first position to the second position before the first step.

12. A method of inspecting a part of a machine, the method comprising:
    cooling a boroscope sheath using the method of claim 8;
    moving a boroscope sheath from the first position to the second position; and
    inspecting a part of the machine through a hole in the boroscope sheath with a boroscope.

13. The method of claim 8, wherein the first step is finished and the second step is started when a temperature of the boroscope sheath is below 100 degrees Celsius.

14. A method of manufacturing a boroscope sheath for a machine, the method comprising:
    providing an elongate tube extending from a front end of the boroscope sheath to a back end of the boroscope sheath, the elongate tube having a wall extending from the front end to the back end and extending around a central bore, the central bore being configured and arranged to allow removable insertion of a boroscope into the central bore;
    providing a plurality of cooling channels which extend in the wall, the plurality of cooling channels including a gas cooling channel configured to circulate gas and a liquid cooling channel configured to circulate gas and liquid; and
    providing a holder to hold the boroscope sheath in a first position relative to the machine when the machine is in use and to move the boroscope sheath to a second position relative to the machine for inspection, wherein at least part of the boroscope sheath is configured and arranged to remain in the machine during use of the machine, and wherein at least part of the boroscope sheath is manufactured using selective laser melting.

* * * * *